(12) United States Patent
Hyman et al.

(10) Patent No.: US 6,596,532 B1
(45) Date of Patent: *Jul. 22, 2003

(54) DEVICE FOR ISOLATION AND SURFACE CULTURE OF MICROORGANISMS FROM BULK FLUIDS

(75) Inventors: Jones M. Hyman, Durham, NC (US); Paul M. Matsumura, Cary, NC (US); Scott R. Jeffrey, Raleigh, NC (US); Martin J. Maresch, Willmar, MN (US); Thurman C. Thorpe, Durham, NC (US)

(73) Assignee: bioMérieux, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,324

(22) Filed: Feb. 11, 2000

Related U.S. Application Data

(63) Continuation-in-part of application No. 09/320,386, filed on May 27, 1999, now Pat. No. 6,197,577, which is a continuation of application No. 08/989,560, filed on Dec. 12, 1997, now Pat. No. 5,976,827.

(51) Int. Cl.$^7$ .............................. C12M 1/34; C12Q 1/02; C12Q 1/04; C12N 11/02; C12N 11/08
(52) U.S. Cl. ........................ 435/287.8; 435/29; 435/34; 435/177; 435/178; 435/180; 435/287.1; 435/288.1
(58) Field of Search ............................. 435/29, 34, 177, 435/178, 180, 987.1, 287.8, 288.1, 289.1

(56) References Cited

U.S. PATENT DOCUMENTS

| | | | | |
|---|---|---|---|---|
| 4,565,783 | A | 1/1986 | Hansen et al. | 435/299 |
| 5,605,812 | A | 2/1997 | Zomer | 435/38 |
| 5,912,115 | A | 6/1999 | Hyman et al. | 435/4 |
| 5,976,827 | A | 11/1999 | Jeffrey et al. | 435/34 |
| 6,153,400 | A | 11/2000 | Matsumura et al. | 435/32 |
| 6,197,577 | B1 | 3/2001 | Jeffrey et al. | 435/288.7 |
| 6,251,624 | B1 | 6/2001 | Matsumura et al. | 435/34 |

FOREIGN PATENT DOCUMENTS

| | | |
|---|---|---|
| DE | 4206850 | 3/1992 |
| DE | 4206856 | 3/1992 |
| DE | 4206857 | 3/1992 |
| DE | 4418818 | 7/1993 |
| DE | 4333056 | 9/1993 |
| DE | 19512824 | 2/1995 |
| DE | 19543368 | 11/1995 |
| DE | 19646484 | 11/1995 |
| EP | 261676 | 9/1986 |
| EP | 842952 | 11/1996 |
| FR | 2514366 | 4/1983 |
| JP | 7128813 | 1/1969 |
| JP | 09019282 | 7/1995 |
| JP | 09075062 | 9/1995 |
| JP | 09075063 | 9/1995 |
| SU | 1766494 | 10/1990 |
| WO | WO 8202563 | 1/1981 |
| WO | WO 8808448 | 4/1987 |
| WO | WO 9312218 | 12/1991 |
| WO | WO 9409151 | 10/1992 |
| WO | WO 9638533 | 6/1995 |
| WO | WO 9822513 | 11/1996 |
| WO | WO 99/29831 | 6/1999 |
| WO | WO 00/03035 | 1/2000 |

*Primary Examiner*—David M. Naff
(74) *Attorney, Agent, or Firm*—Samir R. Patel; Gregory Muir

(57) ABSTRACT

A device and method are provided for isolating and culturing microorganisms from a bulk fluid sample. The device comprises a container having therein a polymeric immobilization layer having interstitial spaces between polymer chains such as a gel matrix. The interstitial spaces are of an average size less than an average size of microorganisms to be separated from the sample and cultured. A bulk fluid sample is applied to the immobilization layer where fluid is absorbed by the layer and microorganisms remain on the surface of the layer. After culturing, microorganism colonies are readily accessible on the surface of the layer for harvest and testing. The immobilization layer may contain one or more of nutrients for microorganism growth, lytic agents, lytic enzymes, antibiotics, antibiotic neutralizers, indicators, detergents and selective agents. An adjacent support layer may be above and/or below the immobilization layer. The immobilization layer may be in combination with a sensor layer that changes color in areas corresponding to portions of the layer having microorganisms thereon. A membrane may be embedded in the immobilization layer for enhancing microorganism visibility and facilitating microorganism harvest.

26 Claims, 8 Drawing Sheets

∿∿∿ =liquid

▨ =gel

○○○ =microorganisms

⸨⸩⸨⸩ =polymer network

⋮⋱⋮ =molecules and small particles

DEVICE FOR ISOLATION AND SURFACE CULTURE OF MICROORGANISMS FROM BULK FLUIDS

CROSS-REFERENCE TO RELATED APPLICATIONS

This application is a continuation-in-part of U.S. application Ser. No. 09/320,386 filed on May 27, 1999, now U.S. Pat No. 6,197,577, which is a continuation of U.S. application Ser. No. 08/989,560 filed on Dec. 12, 1997, now U.S. Pat. No. 5,976,827.

BACKGROUND OF THE INVENTION

This application is related to U.S. patent application Ser. No. 08/989,560 to Jeffrey et al. filed Dec. 12, 1997, and U.S. patent application Ser. No. 09/113,929 to Maresch et al. (now U.S. Pat. No. 5,912,115), the subject matter of each being incorporated herein by reference.

The presence of microbial contamination in clinical specimens is conventionally determined by culturing the specimens in the presence of nutrients and detecting microbial activity through changes in the specimen or in the atmosphere over the specimen after a period of time. For example, in the U.S. Pat. No. 4,182,656 to Ahnell et al., the sample is placed in a container with a culture medium comprising a carbon 13 labeled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of gas in the container. U.S. Pat. No. 4,073,691 provides a method for determining the presence of biologically active agents, including bacteria, in a sealed container containing a culture medium by measuring changes in the character of the gaseous atmosphere over the specimen after a period of time.

A method for non-invasive detection is taught by Calandra et al., U.S. Pat. No. 5,094,955, where a device is disclosed for detecting the presence of microorganisms in clinical specimens, such as blood or other body fluids, and in non-clinical specimens, by culturing the specimens with a sterile liquid growth medium in a transparent sealed container. The presence of microorganisms is determined by detecting or measuring changes in the pH of the specimen or the production of carbon dioxide within the specimen using a sensor affixed to the interior surface of the container or to the sealing means used to seal the container. In Calandra et al., microorganisms can be detected in the presence of interfering material, such as large concentrations of red blood cells, through non-radiometric and non-invasive means.

One disadvantage of the detection system of Calandra et al., is that the time required for detecting the presence of microorganisms is related to the number of microorganisms within the sample. Also, the growth medium for the microorganisms is a liquid, such that the container must usually be agitated during incubation. This involves the additional expense in making the incubation equipment, as well as an increase in the likelihood of a mechanical breakdown. Also, such a system allows for the determination of the presence of microorganisms, but does not allow for enumeration. Furthermore, it is often the case that after detection of microorganisms, it is desired to identify the microorganisms and/or determine their susceptibility to various antibiotics. In a Calandra-type system, it would be necessary to plate out the microorganisms from the liquid culture medium to assure isolation of mixed species before performing susceptibility or identification tests. This involves additional time (time that is not always available if the patient is very ill). Also, a Calandra-type system could not serve the additional functions of reading/imaging plates for antibiotic susceptibility and/or microbial identification.

There are also known methods for detecting microorganisms where a sample is plated onto a gel (agar) plate. In such methods, a sample is swabbed or "streaked" across the gel plate and microorganism growth is determined by viewing the plate to see if any growth occurs where the sample was swabbed on the gel. Though this type of detection is desirable for its surface colonies (which can be immediately tested for antibiotic susceptibility and/or microbial identification), it is undesirable in that it can not handle the large sample volumes required by many procedures such as blood culture.

Some conventional systems that facilitate simultaneous microbial culture and isolation from bulk liquid involve the use of dehydrated granular gelling medium, or a liquid gelling component that forms a gel after the microorganisms are introduced. In either case, the microorganisms are trapped throughout the medium, not just on the surface. This complicates the harvest of microorganisms for further testing.

Surface culture of microorganisms from a liquid sample can be done on a standard semisolid media such as agar. However, such media are too rigid to swell substantially, and can only absorb a volume of liquid that is typically less than 5% of the starting gel volume. Filtration methods can capture microorganisms from larger volumes of liquid, but have a number of disadvantages, which include increased hands-on time, high cost of materials, risk of contamination, and difficulty with particulate containing samples.

SUMMARY OF THE INVENTION

In the present invention, a "bulk" fluid sample, possibly containing microorganisms, is poured or otherwise applied to the surface of a gel matrix. The fluid in the sample is absorbed by the gel, yet microorganisms are retained at the surface. After incubation, mutually isolated microorganism colonies are readily accessible on the surface of the medium for harvest and further testing. This provides the advantage that microorganism culture and isolation from a bulk fluid, previously done as a two step process, can be accomplished in a single step, cutting one or more days from the time required to attain a clinically relevant result. Another advantage is that, with localized microorganism growth, the metabolic changes in the culture environment caused by microorganism growth are also localized, which makes detection of these changes, and hence the microorganisms themselves, easier and faster.

The gel matrix of the present invention is preferably composed of a polymeric material that, by nature and/or fabrication technique, offers a unique set of properties. The gel matrix is sufficiently absorptive to draw in the excess fluid from the sample, but with a small enough pore size to filter out or ensnare microorganisms at the surface. The fluid in the sample is absorbed by the gel with sufficient rapidity that, on a time scale typically ranging from a few minutes to a few hours, multiplying microbes form discrete colonies rather than spreading across the surface of the medium.

While the range of polymers (in the preferred embodiment) appropriate for this invention that are useful as starting materials is practically infinite, the physical properties useful to the present invention are well defined. The polymer must 1) form a gel or highly viscous solution wherein bulk flow of fluid is arrested under the test conditions, 2) absorb fluid from an aqueous solution or suspension without losing cohesion, 3) retain microorganisms to be cultured on or near the surface and largely immobilized, and 4) permit the growth of the microorganisms of interest. Gel matrices of the present invention that are fabricated from a variety of polymeric materials have been shown to have all of these properties, and will isolate and grow microorganisms from sample volumes several times greater, per unit area, than is possible with agar plates.

The device of the present invention comprises a container and within the container an immobilization layer made of an interconnected network of polymer chains, wherein interstitial spaces between the interconnected network of polymer chains are of a size on average less than an average size of microorganisms to be cultured, such that substantially all (or all) of the microorganisms in a sample during culturing are immobilized on the surface of said immobilization layer. A volume of at least 0.04 ml per each square centimeter of surface area of the immobilization layer can be added and absorbed by the immobilization layer, while maintaining microorganism colonies on the surface of the immobilization layer. The bulk fluid sample can be whole blood (or some fraction), other body fluid, manufacturing fluid, food sample, or the like.

DETAILED DESCRIPTION OF THE PREFERRED EMBODIMENT

Figure 1:
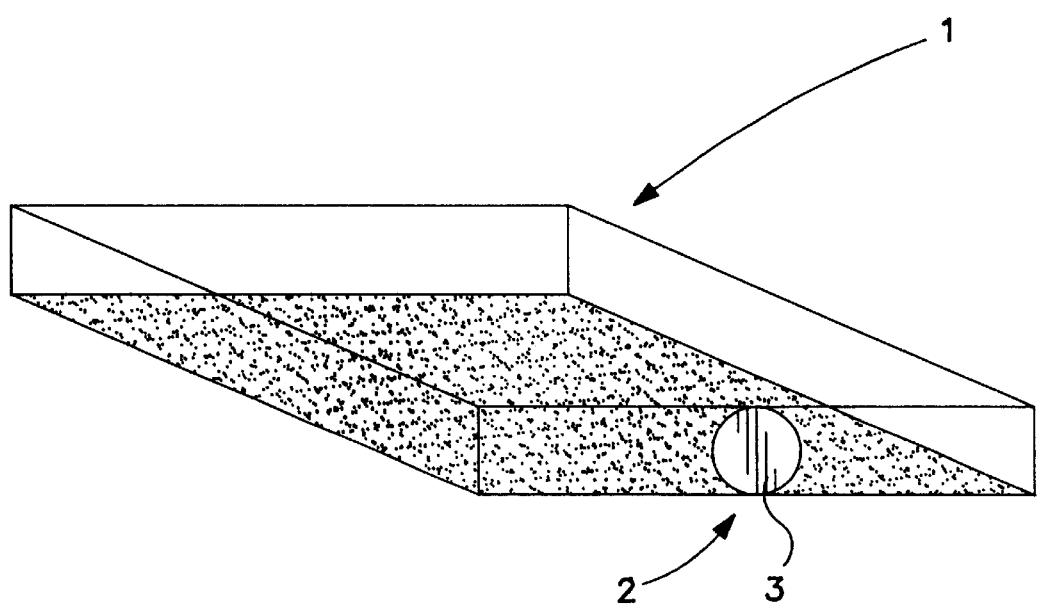
FIG. 1 is an illustration of one embodiment of the device for surface culture of microorganisms.

FIG. 1 is an illustration of sensor plate 1 that can be in the form of a flat, shallow container with at least one side (e.g. the bottom side) being transparent or translucent. Though the container can be open (or even simply a substrate), it is preferably a sealed or sealable container, and preferably with an amount of headspace above the sensor plate layers. The container can be provided with a port 2, which may be sealed with a stopper 3, screw-cap, septum, or any combination thereof (or any other sealing device). Once a sample is collected into the container, the sensor plate can be configured as either a gas-permeable or a gas-impermeable container, depending on the growth requirements of the microorganism. This configuration is accomplished by using different plate composition materials, laminates (gas impermeable and/or hydrophobic gas-permeable membranes), and/or configurable vents (e.g. a gas permeable membrane in an opening of the container wall).

Figure 2:
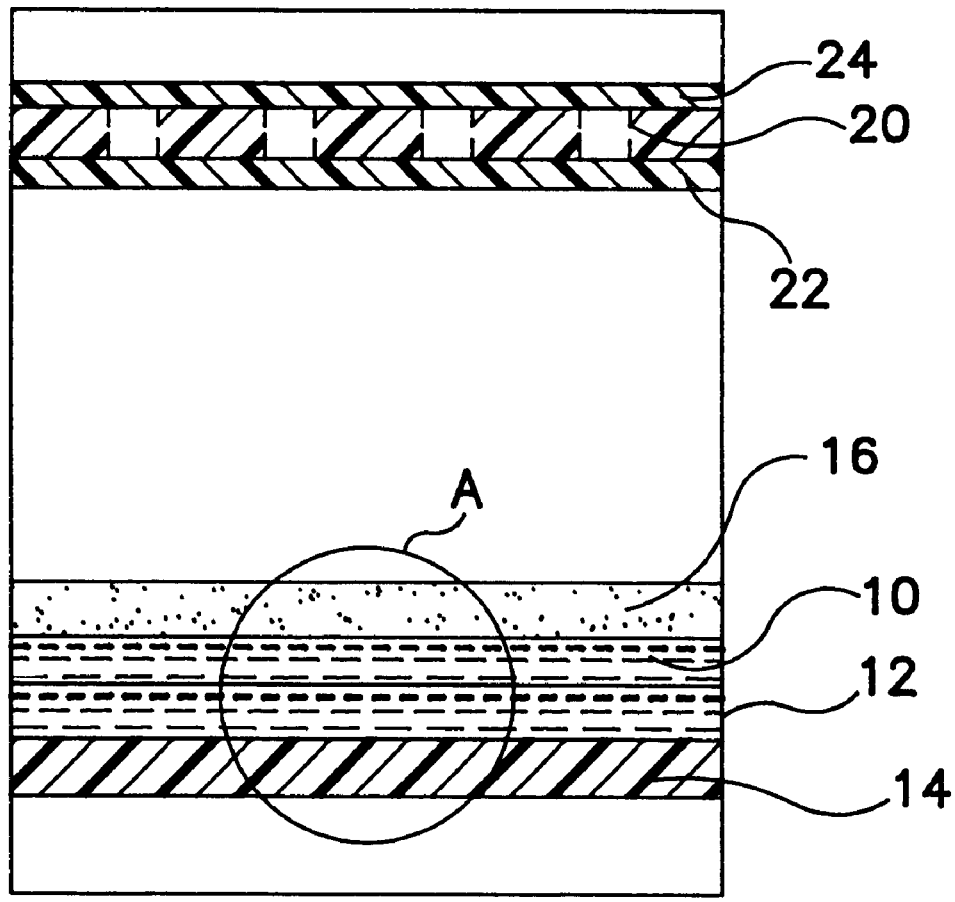
FIG. 2 is a cross section of the device of FIG. 1.

Within the container of the sensor plate device, are one or more layers which help to immobilize/absorb the sample so that colonies of microorganisms can grow localized, which increases the ability to detect the colonies of microorganisms. In one embodiment, at least one layer in the device has matrixes that adversely affect visualization of microorganisms. As can be seen in FIG. 2, provided are an immobilizing layer 10 (matrix layer which fully immobilizes or at least localizes a test sample) and a sensor layer 12. These two layers, which will be described more fully hereinafter, can also be combined together into a single layer, though it is preferred that the two layers be provided separately (assuming a sensor layer is provided at all). As also shown in FIG. 2, is the plate bottom 14, which is preferably transparent for viewing/imaging changes in the sensor layer due to microorganism growth.

The optional sensor layer 12 can be provided for the purpose of indicating the location of microbial growth by providing a tightly localized dramatic change in the ultraviolet, visible, and/or infrared spectrum. This localized change is detectable on the bottom surface of the plate, opposite the sensor surface near the microbial growth. The sensor layer comprises a material that undergoes a change in a detectable property (e.g. an indicator) which is embedded on and/or in a matrix (support material) which is preferably opaque. By "opaque", it is meant that the sensor layer sufficiently blocks the viewing or detecting (in any relevant electromagnetic region) of the test sample and/or actual microorganism colonies immobilized in the immobilization layer from the opposite side of the sensor layer (e.g. semi-opaque, substantially opaque, or fully opaque). Though it is possible to have a transparent or relatively transparent sensor layer if the test sample is also substantially transparent (in which case the sensor layer undergoes localized changes from transparent to opaque in the presence of microorganism colonies), it is preferred that the sensor layer not be transparent Improved results are obtained in detecting microorganisms in test samples that could interfere with detection and enumeration if the sensor layer is opaque. If the test sample itself interferes with visualizing/detecting (e.g. with the eye or with an instrument) the presence or growth of microorganisms directly in the immobilization layer, then it is preferable that at least one of the immobilization layer or the sensor layer (preferably the sensor layer) is capable of blocking detection/visualization of the actual test sample and/or actual microorganisms, and instead detect changes in the sensor layer which correspond to presence/ growth of microorganisms in the immobilization layer. The immobilization layer can also be opaque, and in one embodiment of carrying out the invention, the sensor layer, the immobilization layer, and the sample are all opaque.

The sensor comprises a solid composition or membrane, with an indicator medium immobilized on or within it. The sensor layer is preferably located flush against the inside surface of the container, or in the sealing means used to seal the container or attached to the sealing means, such that the sensor layer is visible from outside. It is preferably affixed to the container to prevent cells, proteins, other solids or other opaque or colored components from getting between it and the container surface. In certain embodiments the sensor layer is separated from the specimen and its growth medium by a membrane or other solid layer.

The sensor is useful in that: 1) changes in the sensor layer due to microbial metabolism (e.g., increases or decreases in a gas component due to metabolism) are detected from the solid or semi-solid immobilizing layer rather than in the atmosphere over the specimen, 2) because the sensor is affixed to the interior surface of the plate or the closure or sealing means or attached through the outside of the closure or sealing means, measurements can be made from outside the transparent wall of the plate or the sealing means without having to violate the integrity of the plate, 3) the external measurements can be made by visual inspection or with an instrument that measures by reflectance, fluorescence, etc., or by image capture, 4) opaquecolored or fluorescent components in the specimen do not interfere with the ability to detect changes or the measurement of those changes, and 5) a high concentration of indicator molecules can be maintained within a small volume in the sensor (e.g., within the polymer emulsion or on the membrane), such that a change can be easily observed or detected.

The nutritional components that make up a complex microbial medium influence the metabolic pathways used by microorganisms. Organic acids, bases and various gases are produced in proportions dependent on the nutrients available. These products also vary from species to species of microorganism. The presence of these products in the immobilizing layer can change its pH. The sensor layer used in the invention could contain pH sensitive indicators that give a measurable change in response to a pH change. Or, the presence of gases that affect the pH of the indicator, such as $CO_2$, could be measured. Microbial growth can also be detected by measurement of changes in $O_2$ and/or fluorescence. The sensor layer can be designed to respond to decreases in $O_2$ concentration due to metabolism of microorganisms. And an indicator could be selected that undergoes a change in fluorescence rather than a change in color or other parameter. Carbon dioxide is a common metabolite produced by most organisms and, therefore, is the preferred metabolite for detection of microbial growth. Whatever mechanism is utilized, in a preferred embodiment, the sensor layer will undergo a detectable change in response to the presence/growth of most microorganisms.

The indicator can be attached either covalently or non-covalently to a support medium. Alternately, the indicator can be encapsulated within a polymer matrix such as being emulsified within a polymer matrix prior to curing.

A variety of different fluorescent and visible pH indicators can be used as the active molecular species in pH, $H_2$, $H_2S$, $NH_3$, $O_2$ or $CO_2$ sensors. Generally, the only limitations on the selection of indicators are the requirements that they have acceptable dynamic ranges and wavelength changes that are detectable by infrared, fluorescence, reflectance and/or imaging technologies.

Sensors for detecting pH changes in the culture medium according to the invention preferably exhibit a change in fluorescence intensity or visible color over a pH range of about 5.0 to about 8.0.

Indicators for a $CO_2$ sensor should exhibit a change in infrared intensity, fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. Indicators belonging to the xanthene, phenolphthalein and phenolsulfonphthalein groups are useful. Examples of these include fluorescein, coumarin, phenolphthalein, thymolphthalein, bromothymol blue, thymol blue, xylenol blue, ortho cresolphthalein and α-naphthol benzein.

The support medium can be a substance such as cellulose or certain silicones, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with microbial growth medium.

The pH indicator sensors directly detect pH changes due to the pH environment of the microbial growth medium. However, these sensors can be made to selectively react to gases (e.g., carbon dioxide, ammonia, hydrogen, hydrogen sulfide, or oxygen) due to microorganism metabolism. A selectively semi-permeable composition or membrane could be provided on the sensor layer, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In one embodiment, the $CO_2$ sensor is comprised of a plurality of components. The first component is a visual or fluorescent pH indicator, which is reactive at the pH range between 6 and 10. Examples of indicators meeting these criteria are bromothymol blue, thymol blue, xylenol blue, phenolphthalein, ortho cresolphthalein, coumarin, and fluorescein. A second component, if necessary, is an acid, base or buffer, which maintains an optimal pH environment for detection of $CO_2$ by the selected pH indicator. A third component can be glycerol or an equivalent emulsifier, which can produce droplets of indicator solution emulsified within the uncured polymer. A fourth component can be a pigment, such as titanium oxide, zinc oxide, magnesium oxide, ferrous oxide, etc. A fifth component can be an uncured polymer such as silicone, which maintains a proper environment for the indicator. Any polymer can be used that does not affect too greatly the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the various components and the polymer is cured to form a semipermeable matrix around the droplets of pH indicator, which permits selective diffusion of $CO_2$ and other gases from the immobilization layer, resulting in localized measurable changes in the sensor layer. The sensor layer can be prepared separately, such as in a mold, cured, and then attached to the plate with an appropriate adhesive, such as a silicone adhesive. Alternatively, and preferably, the sensor is formed on the bottom of the container and cured in situ. After curing, the container with the sensor can be sterilized, such as by autoclaving or gamma radiation. Conveniently, the immobilizing and additional optional layers can be introduced into the sensor plate device before sterilization and thus also sterilized by that process.

In a further example, the sensor layer comprises an indicator solution emulsified in a pigmented silicone matrix. The indicator solution is comprised of thymol blue indicator (0.65 g) dissolved into a solution of 0.8 M potassium hydroxide (10.0 ml) and isopropyl alcohol (10.0 ml). The indicator solution (5.0 g) is then mixed with the pigmented silicone components. The pigmented silicone matrix is comprised of Sylgard 184 silicone (components A (50.0 g) and B (5.0 g)) and white pigment (part # 61-18000, Ferro Corp., New Jersey) (1.0 g). The sensor material is then poured and spread onto a plate in a thin layer (approximately 0.2 to 0.5 mm).

In another example, the sensor layer comprises an indicator solution mixed with a pigmented silicone matrix. The indicator solution is comprised of ortho-cresolphthalein indicator (2.0 g) dissolved into a solution of isopropyl alcohol (5.0 ml) and 0.9 M potassium hydroxide (5.0 ml). The indicator solution (2.5 g) is then mixed with the pigmented silicone components. The pigmented silicone matrix is comprised of Sylgard 184 silicone (components A (25.0 g) and B (2.5 g)) and white pigment (part # 61-18000, Ferro Corp., New Jersey) (0.5 g). The sensor material is then poured and spread onto a plate in a thin layer (approximately 0.2 to 0.5 mm). In a variation of this example, the above ortho-cresolphthalein sensor layer is covered with an overcoat layer comprising the pigmented silicone matrix.

In still another example, the sensor layer is composed of an indicator solution mixed with a pigment solution and a silicone matrix. The indicator solution is comprised of ortho-cresolphthalein indicator (2.0 g) dissolved into a solution of isopropyl alcohol (10.0 ml), and 0.8 M potassium hydroxide (10.0 ml). The pigment solution is comprised of silicone oil (40.0 g), white pigment (part # 61-18000, Ferro Corp., New Jersey) (4.0 g). The silicone matrix is comprised of Wacker Elastosil RT 601 silicone (components A (200.0 g) and B (20.0 g)) and toluene (40.0 g). The indicator solution (20.0 g) is then mixed with the pigment solution (40.0 g) and silicone components. The sensor material is then sprayed onto a plate in a thin layer (approximately 0.1 to 0.3 mm thick).

In addition to indicators responsive to changes in oxygen, carbon dioxide and pH, as mentioned above, indicators could also be utilized that detect changes in ammonia, oxidation-reduction potential, hydrogen, hydrogen-sulfide, or any other substance that undergoes a change due to the presence or growth of microorganisms. Also, a plurality of different indicators could be used in the sensor layer (or in a plurality of sensor layers).

The sensor layer is preferably opaque so as to prevent properties of the sample (e.g. natural fluorescence, opacity, etc.) from affecting or masking the response of the sensor. The sensor layer preferably changes from one opaque state to another opaque state in the presence of microorganisms, with the change being a detectable change by image capture and processing. As one example, the sensor layer could be an emulsified mixture of ortho cresolphthalein indicator in a white pigmented silicone matrix, with an overlay of white pigmented silicone. Or, the sensor layer could be a pigmented silicone matrix emulsified with one or more indicators such as thymol blue indicator, a xylenol blue indicator, or a "universal" indicator. The matrix in the sensor layer could be a suitable latex, polyurethane, nylon membrane (e.g. charged nylon membrane) or cellulose powder. The sensor layer matrix could also be a silicone matrix, such as Sylgard 184, Wacker 601, or Wacker 934. Or, the sensor layer could be made up of two layers, such as an indicator layer and an opaque layer.

The other main layer in the sensor plate device is the immobilizing layer 10. The immobilization layer in the present invention can be provided alone or in combination with other layers, such as the sensor layer described above.

The purpose of the immobilizing layer is to immobilize organisms in the sample on the surface of a matrix. The sample itself can be a liquid or a suspension. The sample could be applied onto an already gelled matrix, or onto a dehydrated or partially dehydrated gel matrix so as to immobilize the microorganisms on the surface of the gel. A gelling agent could also be imbedded in a support matrix to add physical support. Examples include glass, cellulose, or synthetic polymer fibers either mixed throughout or in the form of woven or non-woven fabrics.

More than one gelling agent could be utilized in the sensor plate device, either mixed together or as separate layers. For example, a mixture of guar gum and xanthan gum, combined by weight at an approximate ratio of 2:1, could be used. Other gelling agents could be used singly or in combination, including natural and synthetic hydrogel powders. One or more gelling agents could be combined together selected from gums, agars, agaroses, carageenans, bentonite, alginates, collagens, gelatins, fused silicates, water soluble starches, polyacrylates, celluloses, cellulose derivatives, polyethylene glycols, polyethylene oxides, polyvinyl alcohols, dextrans, polyacrylamides, polysaccharides or any other gelling or viscosity enhancing agents.

Dehydrated and/or partially dehydrated gel matrices could be used for surface colony isolation/immobilization, including one or more synthetic or natural hydrophilic polymers. If more than one gelling agent is used, such could be mixed together or provided in a plurality of layers. In one example, an upper layer could be provided primarily to trap microorganisms on the surface, and a lower layer could be provided as an enhanced absorbent to draw the liquid sample through the upper layer (e.g. a thin agar layer over a modified cellulose, synthetic polymer or hydrogel.

If a sensor layer is used, the immobilization layer must not adversely affect the sensor layer. If the sensor layer undergoes a detectable change due to a pH change, then a very acidic gel layer could adversely affect the sensor layer (also some manufacturing processes are acidic and could leave an acid residue that could adversely affect the sensor layer). Furthermore, it should be certain that this layer does not turn acidic when mixed with a sample, as this could also cause the sensor layer to change even in the absence of microorganisms.

As can further be seen in FIG. 2, an optional conditioning layer 16 can be provided on (or within or below) the immobilizing layer. Though illustrated separate from the immobilization layer in FIG. 2, the conditioning materials from the conditioning layer are preferably incorporated into the immobilization layer itself. Conditioning components, whether provided within the immobilization layer or in a separate layer, can include one or more of media for microorganism growth, lytic agents, lytic enzymes, antibiotic neutralizers, surfactants or other materials helpful for improving microorganism detection and/or enumeration capabilities. Conditioning components can also be provided both within the immobilization layer and in a separate layer in the same sensor plate device.

Lytic agents for conditioning can be added for lysing blood cells in the test sample, for allowing for a smoother gel, and/or for better rehydration of the gel. Examples of possible lytic agents include saponin, digitonin, Tweens™, polysorbitan monolaurate, and other surfactants. Lytic enzymes, typically though not necessarily proteolytic enzymes, may be added for digesting cellular material in a blood sample, for making a smoother gel, and/or for better rehydration of the gel. The lytic enzymes for conditioning can include one or more proteases, for example an enzyme mixture derived from *Aspergillus oryzae*, or the like.

Antibiotic neutralizers may be added for conditioning, in particular for faster and/or better recovery of microorganisms in the test sample. One or more of such neutralizers could be selected from resins, gums, and carbon-based materials (e.g. activated charcoal or Ecosorb™), or one of a variety of enzymes to specifically degrade various antibiotics (e.g. beta lactamase).

Media can also be added for conditioning (whether directly to the immobilization layer or separately). Media is added to provide nutrients for the growth of microorganisms. Though many types of media for different types of microorganisms could be used, if the microorganism is an aerobic organism, the media could include, as one example (an exemplary amount of each being listed in parentheses in g/l): tryptone (17), soytone (3), proteose peptone (5), malt extract (2.5), dextrose (2.5) and MOPS (23). If the microorganism is an anaerobic organism, the media could further include the media listed above for aerobic organisms, as well as Hemin (0.005), L-cystine (0.2), Na—m-bisulfide (0.2) and Menadione (0.0005).

For Coliforms, the media could include, as an example, Lactose (5), bile salts #3 (0.8), $K_2HPO_4$ (7), $KH_2PO_4$ (3), $(NH_4)_2SO_4$ (0.5), $MgSO_4$ (0.1), Na—m-bisulfide (0.4) and SDS (0.1). For yeast, mold and other acid tolerant microorganisms, the media could include, as one example, dextrose (10), yeast extract (10), $(NH_4)$ citrate (2) and tartaric acid to a pH of 5.5.

As can be further seen in FIG. 2, a wall of the container can be provided with apertures 20, below which is a hydrophobic gas-permeable film 22, and above which is a gas-impermeable (removable) film 24. Or, the container could be provided with an opening in a wall thereof with the gas-impermeable film and the hydrophobic gas-permeable film adhered together covering the opening. If the organism is anaerobic, the gas-impermeable film would be left in place. However, if the organism is aerobic, the gas-impermeable film would be removed at the time of the addition of a test sample to the sensor plate device. Of course, the hydrophobic gas-permeable film need not be provided at all, though it is beneficial for preventing contaminants from entering the container, and for preventing potentially infectious test material from leaking out of the device.

Figure 3:
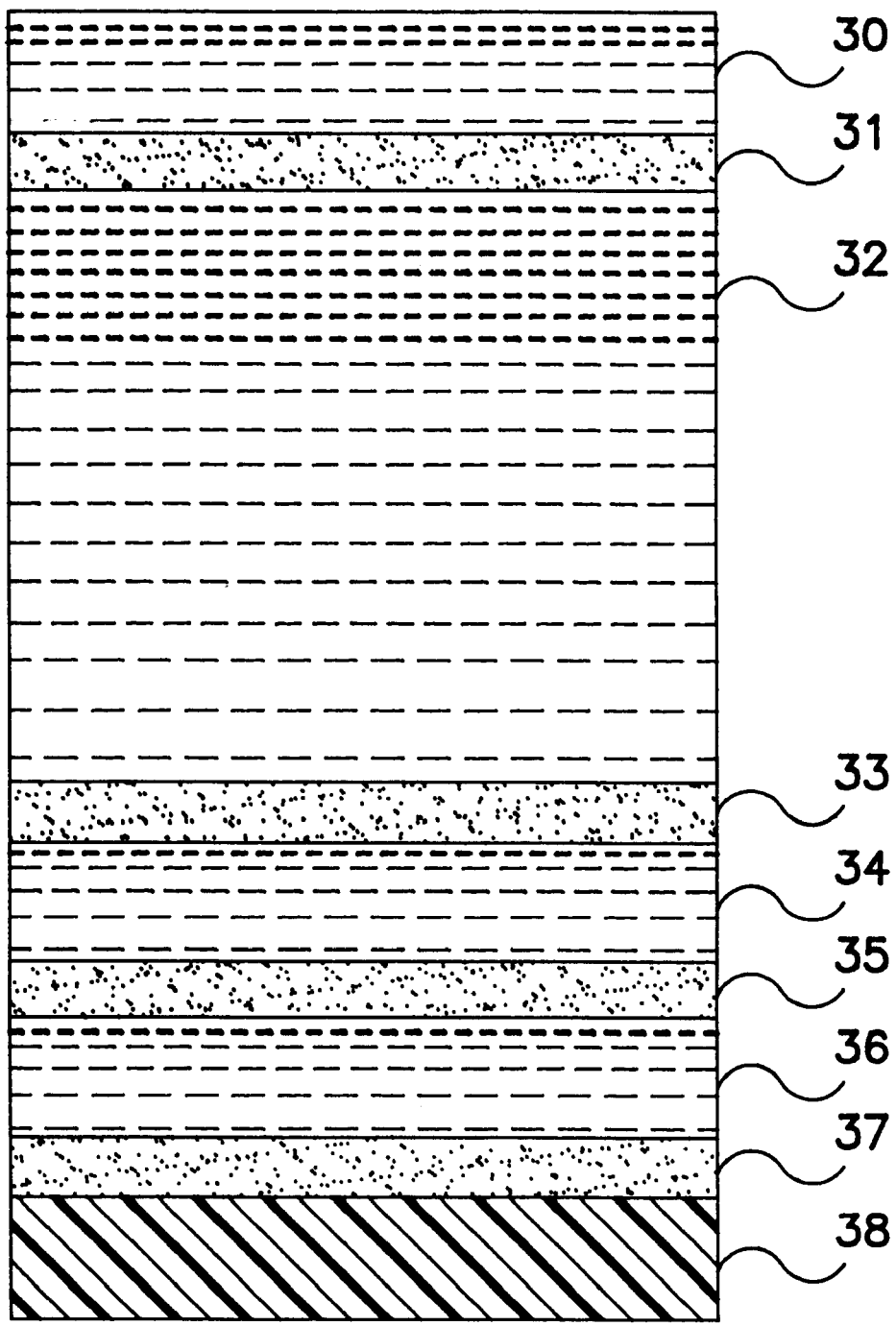
FIG. 3 is a cross section of an alternative embodiment of the surface culture device.
Figure 4:
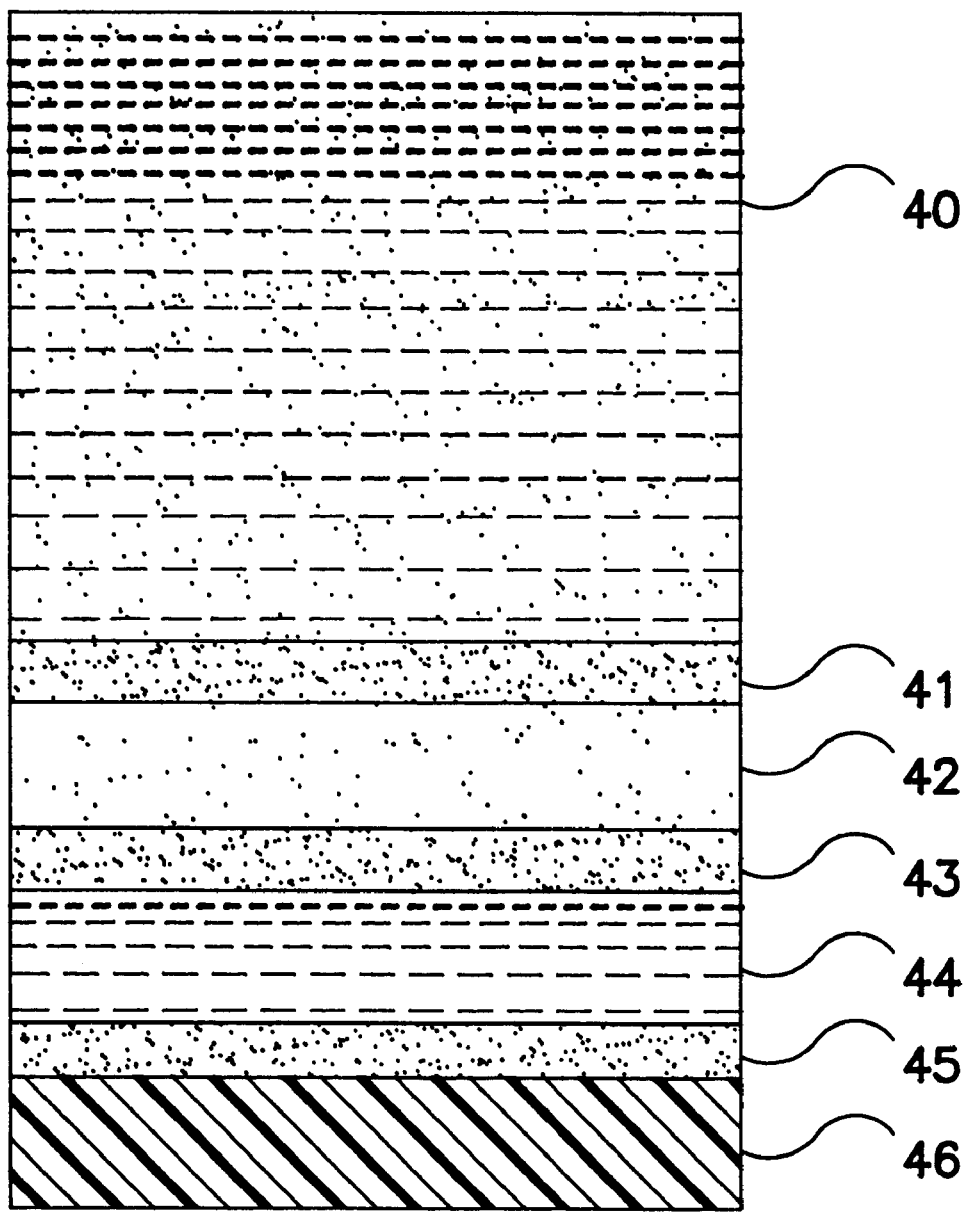
FIG. 4 is a cross section of a further alternative embodiment of the surface culture device.
Figure 5:
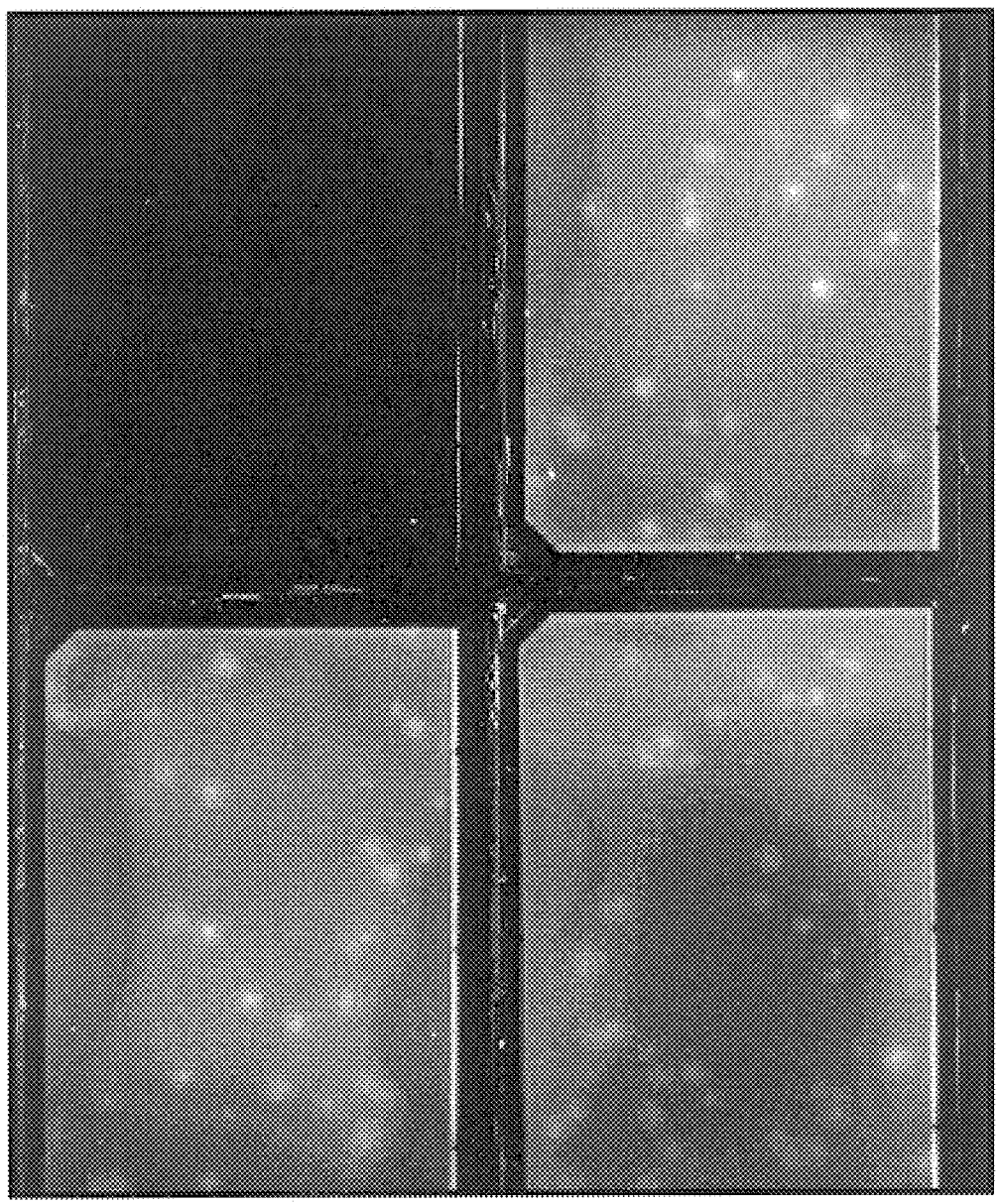
FIG. 5 shows the bottom of three surface culture devices positive for *E. coli;*

Area A in FIG. 2 is illustrated in further detail in FIGS. 3 and 4. As can be seen in FIG. 3, in a further embodiment of the sensor plate device, in place of a single immobilization matrix layer, there can be provided one or more of: an isolation gel layer 30 for a semi-rigid surface to allow surface capture and recovery after growth, an adhesive layer 31, an absorptive gel layer 32 and an additional adhesive layer 33. The absorptive gel layer 32 can include one or more of conditioning components (in gels), media for microorganism growth, lytic enzymes, and antibiotic neutralizers. As can be further seen in FIG. 3, in place of a single sensor layer, there can be provided one or more of: an overcoat layer 34, an adhesive layer 35, an indicator layer 36, and an additional adhesive layer 37 in contact with plate bottom 38.

In an additional embodiment of the invention as illustrated in FIG. 4, provided is a matrix layer 40 which comprises: a dehydrated gelling layer powder, and dry conditioning components such as media, lytic enzymes and antibiotic neutralizers. As in FIG. 3, in place of a single sensor layer, there can be provided one or more of: an adhesive layer 41, an overcoat layer 42, an adhesive layer 43, an indicator layer 44, and an adhesive layer 45 in contact with plate bottom 46.

The size of the sensor plate device can be varied depending upon the desired sample size. In one example, a sensor plate device has an immobilization layer of the dimensions of 74 mm×117 mm. If the immobilization layer comprises a wet-type gel, then the sample size could be made very small (e.g. 1 ml or less), or, such as with a blood sample, the sample size could be up to 15 ml. On the other hand, if the immobilization layer comprises a dehydrated dry powdered gel, then the sample size could be even greater, depending upon the type amount of the powdered of gel and sample (e.g. the sample could be 30 ml or more).

In use, a fluid sample is introduced into the sensor plate device. The sample is "conditioned" (if desired) as it spreads across the bottom surface of the sensor plate. The sample is absorbed into, an immobilization matrix layer. The sensor plate is then incubated, promoting the growth of microorganism colonies. A sensor layer located toward a bottom surface of the sensor plate device, undergoes a detectable change so as to indicate the presence of microorganism colonies. Finally, the sensor plate device is inspected manually or automatically to determine the presence and location of microorganism colonies.

The instrument performs three main functions on the sensor plate: plate incubation, image acquisition/capture, and image processing. The instrument provides a controlled environment for incubating plates, which can include a heater if incubation is to take place at an elevated temperature from ambient (though an elevated temperature is not necessary in all situations). A fluid sample is added to the sensor plate device, after which the sensor plate is placed in the instrument where it is subsequently sensed/observed by an image acquisition/capture device (e.g. a camera or scanner) during the incubation period.

Images of the bottom of the sensor plate device can be captured at regular predetermined intervals and subsequently analyzed using one or more image processing techniques and algorithms to determine whether a microorganism colony is present on the sensor plate. The image-processing algorithm implemented to detect and enumerate microorganisms is comprised of one or more of the following steps:

a) Image Masking—to isolate the area of interest from extraneous image data;

b) Image Subtraction—to isolate the areas of change between two images taken at different time intervals;

c) Image Equalization—to amplify the magnitude of the changes appearing in the subtracted image;

d) Image Blurring—to reduce the effects of single pixel noise in the equalized image (low pass filter);

e) Image Contrast and Brightness Enhancement—to further amplify localized differences in the filtered image;

f) Image Thresholding (with several thresholds, if required)—to prepare the image for the colony detection/enumeration algorithm; and/or g) Colony Detection, Enumeration, and Classification—to determine the presence of microbial organisms on the plate, to enumerate the number of colonies on the plate, and/or perform color analysis to classify colonies on the plate.

In a preferred embodiment of the invention, the immobilization layer is designed to absorb large volumes of bulk test sample fluid, yet maintain any microorganisms present in the bulk fluid sample, as surface colonies on or near the surface of the immobilization layer. In this case, surface colonies are defined as being accessible from the surface without penetrating the medium, although the colony may actually be partially embedded in the medium. Immediately after primary incubation, isolated colonies of microorganisms are available and easily accessible for harvest and further testing. In it's simplest form, the device comprises the immobilization layer within a container (e.g. on a plate or simple substrate), and in the absence of a sensor layer. The immobilization layer comprises a microporous highly-swellable medium capable of absorbing large volumes of sample fluid.

As formulated for this invention, hydrophilic polymers can form a gel by interstrand entanglement and/or crosslinking of the polymer chains (a polymer chain as used herein denotes a molecular strand of a polymer). In the present invention, surface capture of microorganisms from bulk fluid is made possible because the polymer chains in the gel are formed into a contiguous, microporous, and highly swellable network. The pores, essentially the spaces between the polymer chains, can be sized such that the microorganisms of interest can not penetrate far into the gel, while smaller particles or molecules such as water, salts, proteins, and nutrients pass freely throughout.

Figure 6:
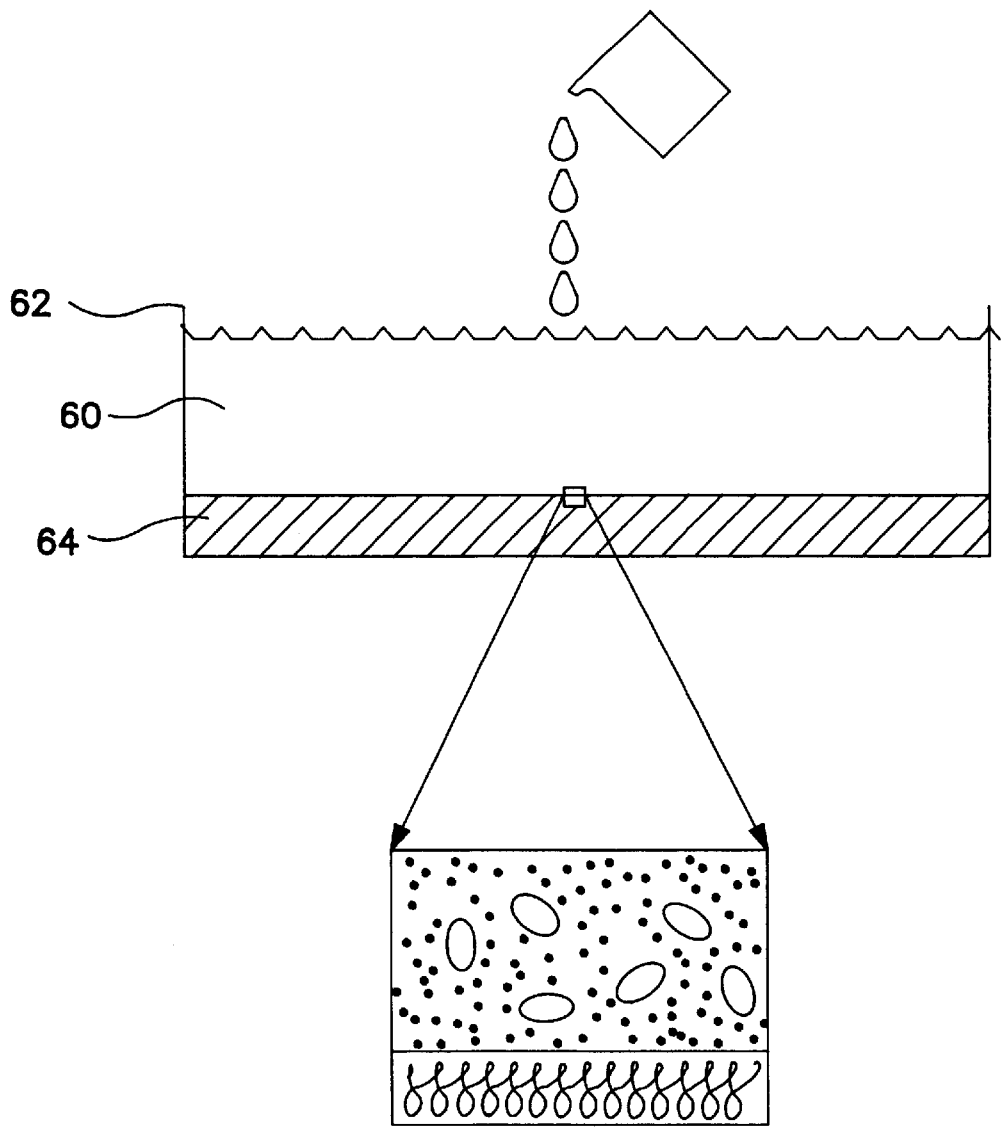
FIG. 6 shows the addition of a bulk liquid sample to the device for surface culture of microorganisms.
Figure 7:
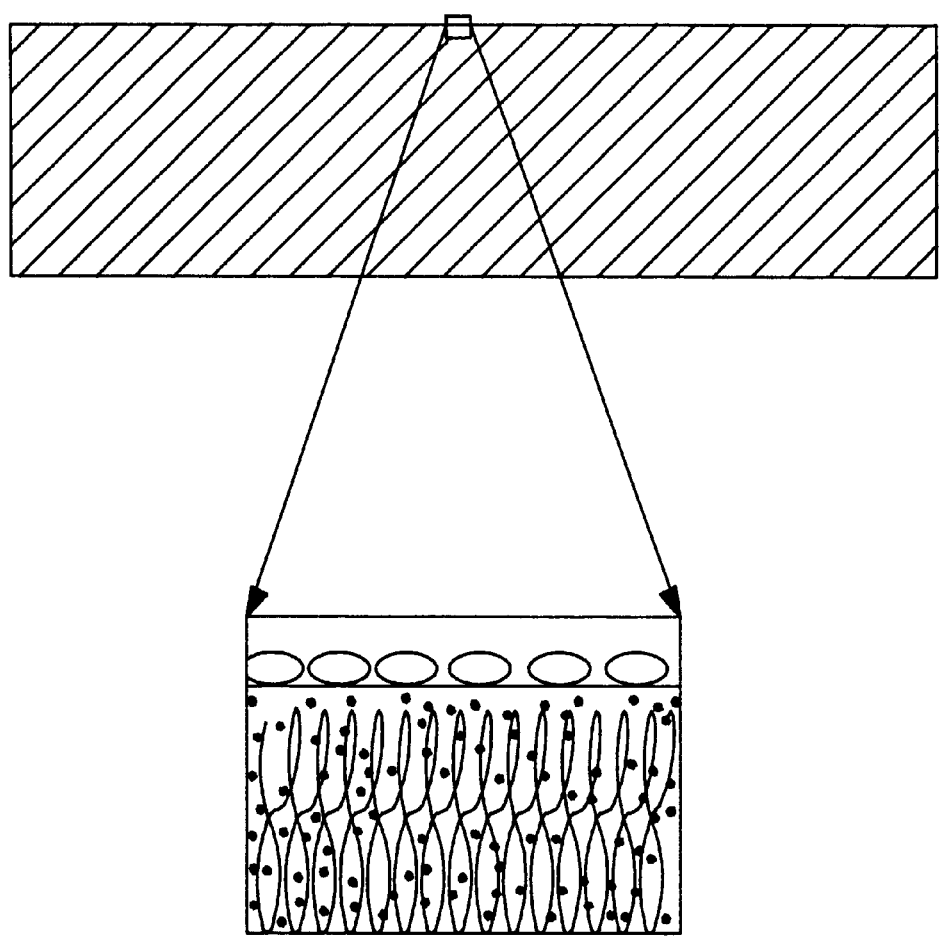
FIG. 7 shows the device of the present invention where the bulk liquid sample has been absorbed with microorganisms remaining on the surface.

The primary component of the immobilization layer in this embodiment is an absorbent culture medium comprised of a hydrophilic polymer network, or hydrogel, that is able to swell substantially to absorb aqueous fluids without losing its semisolid or highly viscous, microporous nature. When an aqueous liquid is applied to the surface of such a polymer network, the liquid diffuses into the network, which expands as a result. Water and molecules or particles smaller than the pore size of the polymer network will diffuse freely throughout the gel. Particles, such as microorganisms, larger than the pore size of the gel are trapped on or near the surface. As can be seen in FIG. 6, a large volume fluid sample 60 to be tested for microorganisms is added to container 62 (having the microporous highly-swellable medium 64 therein). As can be seen in FIG. 7, the microporous medium greatly expands due to absorption of the bulk fluid sample, while the polymer network of the medium remains intact.

The immobilization layer (gel polymer layer) should not inhibit the growth of the microorganism to be detected. While one gelling medium may inhibit the growth of some microorganisms, the same medium may promote the growth of others. Although selective inhibition of certain microorganisms can be used to advantage, in a preferred embodiment of the invention, the gelling medium neither enhances nor inhibits the growth of a broad range of microorganisms, but rather acts as an inert scaffold for microorganism growth. The polymers used to create the gelling medium are preferably hydrophilic. In general, the more hydrophilic the polymer, the faster it will swell with sample fluid. Though less hydrophilic or hydrophobic polymers can be used as part of the matrix to impart desired properties, the bulk of the gelling medium should be hydrophilic.

The gel formed by the polymers must maintain cohesion or high viscosity under conditions of use. The gel must maintain integrity throughout the volume and temperature changes required by its use. It is also desirable that polymers not be readily degradable by the microorganisms being cultured. Also, the interchain crosslinking or entanglement of the gelling polymers must be high enough to maintain gelling or high viscosity, but low enough to allow a high degree of swelling. More particularly, regardless of the material used (natural, synthetic, or semi-synthetic polymers, or other material), it is preferable that there be provided an interconnected network of polymer chains that are sufficiently flexible to absorb liquid without disrupting the network. The interstitial spaces between the interconnected polymer chains are of a size on average less than an average size of microorganism to be cultured, so that substantially all of the microorganisms in the sample being tested are immobilized on the surface of the polymer gel (the "immobilization layer". By interconnected, it is meant that the polymer chains are physically entangled and/or crosslinked.

Based on physical properties, there are two main classes of gelling materials that can be used as the basis of the absorbent culture medium of the present invention, namely rigid gels and soft gels. Each requires a different method of fabrication.

Rigid gels, are usually homogeneously crosslinked and have a gelatin-like consistency. The crosslinking can consist of covalent, ionic, or hydrogen bonds, hydrophobic interactions, or a mixture of any or all of these. This type of gel is generally firm and brittle, but can be made very flexible and swellable for use in the present invention by limiting the amount of crosslinking. Gels of this type would be cast in the final desired dimensions, then dehydrated prior to use. Alternately, the gel could be cast in a dehydrated form such that, after swelling with the fluid sample, it attains the desired shape.

Some natural gelling agents, such as agarose and gelatin, will form rigid gels that have only limited use in the present invention. Once formed, these gels will not swell appreciably upon addition of bulk sample fluid. If dried and subsequently rehydrated, they will not return to their original dimensions. This occurs because of the uncontrolled number of associative crosslinks (hydrogen or ionic bonds) that hold the gel together and form tighter and tighter crosslinks as the gel shrinks on dehydration.

More useful gels for an absorbent medium can be made from polymers that have weaker associative bonds, or whose associative bonds are weakened by chemical modification, but with a carefully controlled number of crosslinks. Gels of this type can be fabricated by a number of processes. Simultaneous free radical polymerization and crosslinking, for example polyacrylamide gels similar to those used in electrophoresis, can be used to produce gels suitable for this invention. Alternately, polymers can be chemically crosslinked after polymerization. Examples of such gels include dextran crosslinked with butanediol diglycidyl ether (BDE), CMC crosslinked with polyvalent cations, gelatin crosslinked with glutaraldehyde (GA), and polyvinyl alcohol crosslinked with GA.

An efficient alternative to chemical crosslinking is crosslinking with radiation. Polymer chains exposed to high energy radiation such as gamma rays or electron beams will spontaneously crosslink through free radicals initiated by the radiation. Almost any polymer can be crosslinked by this process. Hydrophilic polymers such as polyvinyl pyrrolidone (PVP), PEO, and linear polyacrylamide have been shown amenable to this procedure, with the added benefit in this invention of microbial sterilization.

The other type of gel (based on physical properties) that could be used in the present invention is a soft gel. Soft gels have a pudding-like consistency that are found in a continuum ranging from a viscous liquid to a malleable solid, depending on the composition of the gelling medium and its concentration. Such gels have the desirable property that they resist flow under low shear, but can be formed to any shape under sufficient pressure. The properties of a soft gel come about primarily through entanglement of long, often branched, polymer chains.

Most of the natural gums and many non-crosslinked, or minimally crosslinked, synthetic polymers will make soft gels. The fabrication process for these gels would involve either drying of a solution or suspension of the polymers to form a film, or extrusion, stamping or rolling of a partially hydrated polymer paste into the desired form.

The specific type of the polymer material that can be used in the present invention, and whether it is a rigid or soft gel, or whether it is natural, synthetic, or semi-synthetic, is largely unimportant. More relevant are the specific physical properties of the material utilized in the present invention. Polymers that may be useful in the present invention include, but are not limited to, the following: polysaccharides such as xanthan gum, guar gum, locust bean gum, pectin, starch, tragacanth gum, dextran, agar agarose, carrageenan, alginate, and other natural gums, semi-synthetic polymers such as carboxymethylcellulose (CMC) and hydroxyethylcellulose and other cellulose, starch, guar, alginate, chitin and dextran derivatives, synthetic polymers built from any or combinations of monomers including acrylic acid, acrylamide, vinyl-pyrrolidone, vinyl-alcohol, hydroxyethylmethacrylate and numerous other acrylic, vinylic or styrenic based monomers, as well as polyethylene glycol, polyethylene oxide, polypropylene glycol, polybutylene glycol, and copolymers or mixtures of any of the above.

In the preferred embodiment of the invention, the immobilization layer is made of an interconnected network of polymer chains that are sufficiently flexible to absorb large volumes of liquid sample without disrupting the interconnected network, and where the interstitial spaces between the interconnected polymer chains are of a size on average less than an average size of microorganisms to be cultured/detected. Therefore, all or most of the microorganisms in the sample will be immobilized on a top surface of the immobilization layer even if the sample volume is large. Many microorganisms are approximately 0.1 to 1 micrometer in diameter. Therefore, in a preferred embodiment of the invention, the interstitial spaces between the interconnected polymer chains are less than 1 micrometer (e.g. between 0.1 and 1 micrometer), and more preferably less than 0.5 micrometer, and even as small as 0.1 micrometer or less.

A typical agar plate used for culturing microorganisms absorbs approximately 0.02 ml/cm$^2$ or less of the sample fluid added thereto. In the present invention, the interconnected network of polymer chains can absorb fluid sample of from 50% to 400% of the initial volume of the polymer network. In the present invention, fluid volumes can be absorbed greater than 0.04 ml/cm$^2$ (e.g. from 0.04 to 1.0 ml/cm$^2$, or from two to fifty times that of the standard agar plate). In a preferred embodiment, fluid volumes greater than 0.05 ml/cm$^2$, or even greater than 0.1 ml/cm$^2$, such as from 0.1 ml/cm$^2$ to 0.7 ml/cm$^2$ (five to thirty five times that of the standard plate) can be absorbed. In a further preferred embodiment, fluid volumes greater than 0.2 ml/cm$^2$, such as from 0.2 ml/cm$^2$ to 0.4 ml/cm$^2$ (10 to 20 times that of a standard agar plate) can be absorbed. Such volumes of fluid can be absorbed by said immobilization layer within 20 hours, preferably less than 10 hours, or even less than 4 hours (in some embodiments the bulk fluid is absorbed within 15 minutes).

This ability to absorb such large volumes of sample fluid while still maintaining microorganisms on the surface, allows for the use of the culturing/detection device in a wide variety of areas, including the plating of blood directly onto the plate (e.g. direct draw from a patient). Lytic agents and/or enzymes can be dispersed on and/or in the immobilization layer to break open cells in the blood sample. And, if a sample (e.g. a food sample, manufacturing fluid or drinking water) is very dilute, the chances of a microorganism being present in the sample added to the plate are increased as the sample volume plated is increased, thus improving the efficacy of the test.

Figure 8:
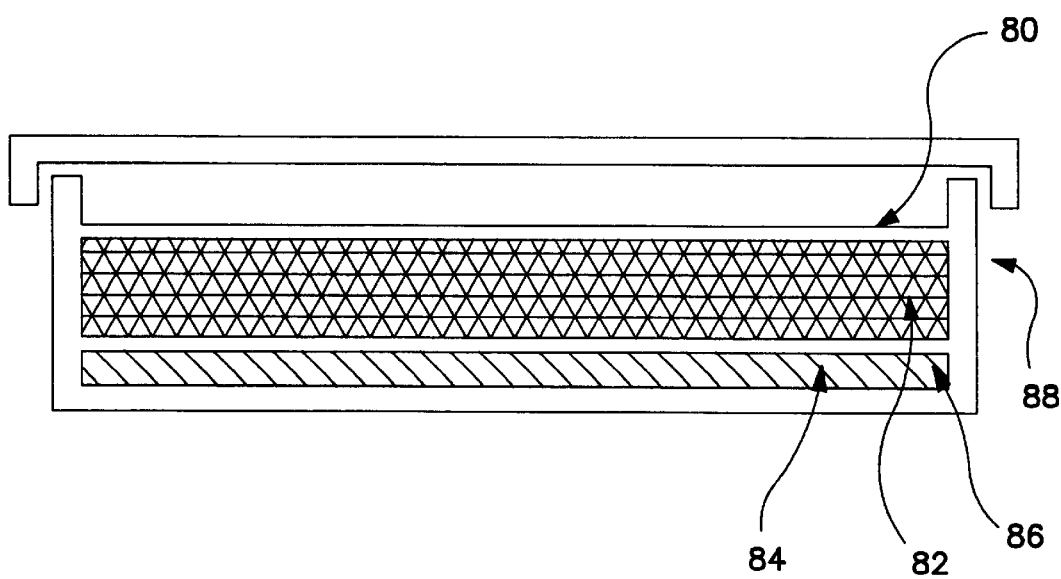
FIG. 8 is a cross section of another embodiment of the present invention.

The immobilization layer may include (in addition to the gel matrix), culture media, antibiotics, antibiotic neutralizers, indicators, detergents, lytic agents, or one or more support matrices (depending upon the ultimate use of the device). A support matrix can be added to add physical strength to the gel layer or aid in fabrication of the device. The support can be a woven or non-woven fabric, a filter membrane or individual fibers, as long as it is porous enough to pass liquid therethrough (liquid passage is necessary if the support is disposed on the top of the immobilization/gel matrix layer, upon which the bulk fluid sample would then be added. The support could also be disposed between the immobilization layer and the sensor layer (if one is provided), or dispersed throughout the immobilization layer. As one example, as can be seen in FIG. 8, a top support layer 80 is disposed on the immobilization layer 82, which is disposed on a second support layer 84, which in turn is disposed on sensor layer 86, all being within container 88.

To date, several different examples of this invention have been tested to show feasibility. The variety of methods demonstrates how this concept can be tailored for a wide range of applications.

EXAMPLE 1

CMC Dried Film

A solution of 1.5% (w/v) carboxymethyl cellulose (CMC, Aldrich Chemical Company, average MW of 700,000) was autoclaved at 121° C. for 15 minutes in liquid cycle. After cooling, the solution was added in 10 ml portions to 60 mm (52 mm inside diameter, 21.2 cm$^2$) petri dishes and dried overnight at 50° C. The temperature was then increased to 80° C. for 1 hour to reduce any bacterial load from contamination.

Sheep blood was spiked with *S. aureus* (ATCC#25923) at a concentration of approximately 10 CFU/ml, and was lysed by the addition of saponin to a final concentration of 0.5% (w/v). The dried CMC films were inoculated with 2.5 ml of the lysed blood solution, covered and incubated overnight at 35° C.

After the overnight incubation, all fluid had been absorbed into the gel and mutually isolated colonies of *S. aureus* were easily observed on, and harvested from, the surface of the gel. There was no visible penetration of the bacteria into the gel, nor were any colonies trapped within the bulk of the gel. In this example, the fluid volume absorbed per unit surface area was 0.12 ml/cm$^2$.

EXAMPLE 2

Polyacrylamide

A pre-polymerization solution for forming light initiated polyacrylamide gels was made with the following composition; Acrylamide/BisAcrylamide (10%T, 0.4%CO, TEMED (0.04% v/v), riboflavin phosphate (0.0025%. w/v), and sodium phosphate (10 mm pH 6.5, final concentration). The solution was added in 20 ml portions to 90 mm (86 mm inside diameter), 58.1 cm$^2$ petri dishes. The petri dishes were stacked and sealed in an anaerobic culture jar with an anaerobic atmosphere generator pack. The anaerobic jar was then placed in the dark for 30 minutes to allow time for the oxygen to be removed before polymerization.

The plates in the jar were then illuminated under a 15 W fluorescent desk lamp at a distance of approximately 10 cm, overnight at approximately 23° C. After polymerization, 5 ml of 10% Glycerol was added on top of each gel, then the gels were dried overnight at 35° C., and baked for 1 hour at 65° to reduce any bacterial contamination.

The gels were partially rehydrated with 10 ml tryptic soy broth (TSB). After the TSB absorbed, the gels were inoculated with an addition 5 ml TSB spiked with *E. coli* (ATCC#25922) at a density of approximately 10 CFU/ml. The inoculated gels were covered and incubated overnight at 35° C.

After the overnight incubation, all fluid had been absorbed into the gel and mutually isolated colonies of *E. coli* were easily observed on, and harvested from, the surface of the gel. In this example, the fluid volume absorbed per unit surface area was 0.26 ml/cm$^2$.

EXAMPLE 3

Xanthan/Guar Paste with Support

A paste was made by combining 10 g of pre-hydrated xanthan gum and 2.5 g of pre-hydrated guar gum, with 50 ml to tryptic soy broth (TSB). Portions of the paste were sandwiched between two layers of a woven nylon support mesh and pressed between plastic plates until 1.5 g of paste formed approximately a 60 mm diameter circles. A 51 mm diameter punch was used to cut our circles of the paste sandwich, which were transferred to a polycarbonate sheet and sterilized by autoclaving. After cooling, the paste circles were transferred to a 60 mm (52 mm inside diameter) petri dishes along with 0.5 ml of TSB to partially hydrate the paste and aid in placement of the disks.

Human blood was collected with SPS as an anticoagulant and spiked with *S. aureus* (ATCC#25923) or *E. coli* (ATCC#25922) at a concentration of approximately 25 CFU/ml. The spiked blood was lysed by the addition of an equal quantity of TSB with 2.0% saponin (w/v). The gum paste disks were inoculated with 5.0 ml of the lysed blood solution, covered and incubated overnight at 35° C.

After the overnight incubation, all fluid had been absorbed into the gel and mutually isolated colonies of *S. aureus* and *E. coli* were easily observed on, and harvested from, the surface of the gel. There was no visible penetration of the bacteria into the gel, nor were any colonies trapped with the bulk of the gel. In this example, the fluid volume absorbed per unit surface area was 0.24 ml/cm$^2$.

EXAMPLE 4

Xanthan/Guar Paste with Charcoal

A paste was formulated according to example 3, except that 10 g of pharmaceutical grade powdered charcoal (an antimicrobial neutralizer) was added to the mix. Paste disks of this formulation were fabricated and inoculated as in example 3. Fluid absorption and organism growth were not noticeably affected compared with example 3.

EXAMPLE 5

Xanthan/Guar Paste with Membrane Filter, Support

Paste disks were fabricated and inoculated as in example 3, except that the upper facing support was a membrane filter (Gelman Supor-450). Fluid absorption was not noticeably affected compared with example 3, yet the surface of the growth medium had a smoother appearance and the bacterial colonies were easier to visualize.

EXAMPLE 6

Xanthan/Guar Paste vs. Agar

A paste was formulated to example 3, except that the paste was composed of 20 g of pre-hydrated xanthan gum, 5 g of pre-hydrated guar gum and 50 ml of tryptic soy broth (TSB). Paste disks of this formulation were fabricated as in example 3, and inoculated with *E. coli* (ATCC#25922) at approximately 25 CFU/ml in TSB. A range of inoculation volumes was tested up to 10.6 ml. At the same time, commercially available 90 mm blood agar plates (86 mm inside diameter, 58.1 cm$^2$) were similarly inoculated with volumes up to 2.0 ml. Both sets of inoculated plates were enclosed in a perforated plastic bag and incubated overnight at 35° C. After the incubation, the plates were removed and examined for fluid uptake and bacterial colonies.

All of the paste disks had absorbed all of the inoculation fluid, as much as 10.6 ml, and bacterial colonies were visible on the surface. On the blood agar plates, the maximum volume absorbed was 1.0 ml. In this example, the paste disks had absorbed 0.50 ml/cm$^2$ while the agar plates had absorbed less than 0.02 ml/cm$^2$.

The foregoing description is sufficient to enable one skilled in the art to practice the invention. The examples herein should not be construed as limiting the scope of the claims in any way. Indeed, various modifications of the invention in addition to those shown and described herein will become apparent to those skilled in the art from the foregoing description and fall within the scope of the appended claims.

We claim:

1. A device for culturing microorganisms in a sample comprising a container and within said container an immobilization layer made of an interconnected network of polymer chains, wherein interstitial spaces between said interconnected network of polymer chains are of a size on average less than an average size of microorganisms in said sample to be cultured such that substantially all of the microorganisms in said sample during culturing are immobilized on the surface of said immobilization layer.

2. The device of claim 1, wherein said interstitial spaces are less than 10 micrometers.

3. The device of claim 2, wherein said interstitial spaces are less than 1.0 micrometer.

4. The device of claim 3, wherein said interstitial spaces are less than 0.1 micrometer.

5. The device of claim 1, wherein said interconnected network of polymer chains is capable of absorbing greater than 0.04 ml of said sample per each cm$^2$ of surface area of said immobilization layer.

6. The device of claim 5, wherein said interconnected network of polymer chains is capable of absorbing greater than 0.05 ml of said sample per each cm$^2$ of surface area of said immobilization layer.

7. The device of claim 6, wherein said interconnected network of polymer chains is capable of absorbing greater than 0.1 ml of said sample per each cm$^2$ of surface area of said immobilization layer.

8. The device of claim 1, further comprising lytic agents and/or enzymes dispersed on and/or in said immobilization layer.

9. The device of claim 1, wherein said immobilization layer is a solid or semi-solid layer.

10. The device of claim 9, wherein said immobilization layer comprises a hydrophilic polymer.

11. The device of claim 1, wherein said immobilization layer comprises nutrients for promoting growth of microorganisms.

12. The device of claim 1, wherein said immobilization layer further comprises at least one of antibiotics, antibiotic neutralizers, indicators, detergents, selective agents, and culture media.

13. The device of claim 1, wherein the immobilization layer comprises a support matrix.

14. The device of claim 1, further comprising a support matrix as an adjacent layer above and/or below the immobilization layer.

15. The device of claim 1, further comprising a sensor layer disposed in said container below said immobilization layer.

16. The device of claim 15, wherein said sensor layer comprises an indicator which causes said sensor layer to change color in areas corresponding to portions of said immobilization layer having microorganisms thereon.

17. The device of claim 15, wherein said sensor layer undergoes a localized change in the ultraviolet, visible and/or infrared spectrum.

18. The device of claim 17, wherein said localized change is detectable through a wall of said container.

19. The device of claim 1, further comprising conditioning agents within said immobilization layer or in a layer on or below said immobilization layer.

20. The device of claim 15, wherein said sensor layer is opaque.

21. The device of claim 1, further comprising a membrane embedded within said immobilization layer for enhancing microorganism visibility and facilitating microorganism harvest.

22. The device of claim 1, wherein said interconnected network of polymer chains are capable of absorbing said sample within a time period such that any microorganisms present in said sample are immobilized on the surface of the immobilization layer as discrete colonies.

23. The device of claim 1, wherein said interconnected network of polymer chains are capable of absorbing said sample within 20 hours.

24. The device of claim 23, wherein said interconnected network of polymer chains are capable of absorbing said sample within 4 hours.

25. The device of claim 24, wherein said interconnected network of polymer chains are capable of absorbing said sample within 15 minutes.

26. The device of claim 1, further comprising a sensor layer disposed within said immobilization layer.

* * * * *